United States Patent
Soga et al.

(10) Patent No.: US 6,323,387 B1
(45) Date of Patent: Nov. 27, 2001

(54) DISPOSABLE BODY FLUIDS ABSORBENT ARTICLE

(75) Inventors: Hiroyuki Soga; Toshio Inoue; Seiji Suzuki; Takaaki Shimada, all of Kagawa-ken (JP)

(73) Assignee: Uni-Charm Corporation (JP)

(*) Notice: Subject to any disclaimer, the term of this patent is extended or adjusted under 35 U.S.C. 154(b) by 0 days.

(21) Appl. No.: 09/287,987

(22) Filed: Apr. 8, 1999

(30) Foreign Application Priority Data

Apr. 9, 1998 (JP) .................................................. 10-097982

(51) Int. Cl.⁷ ........................................................ A61F 13/15
(52) U.S. Cl. ...................... 604/368; 604/370; 604/385.01
(58) Field of Search ...................................... 604/368, 378, 604/385.01, 370

(56) References Cited

U.S. PATENT DOCUMENTS

| 4,699,823 | 10/1987 | Kellenberger et al. | |
|---|---|---|---|
| 5,356,403 | * 10/1994 | Faulks et al. | 604/378 |
| 5,728,082 | * 3/1998 | Gustafsson et al. | 604/368 |
| 5,741,241 | * 4/1998 | Guidotti et al. | 604/368 |
| 5,800,419 | * 9/1998 | Soga et al. | 604/368 |

FOREIGN PATENT DOCUMENTS

| 2 627 080 A | 8/1989 | (FR) . |
| 0 558 889 A | 9/1993 | (EP) . |
| 0 692 231 A | 1/1996 | (EP) . |

* cited by examiner

*Primary Examiner*—Dennis Ruhl
(74) *Attorney, Agent, or Firm*—Baker & Daniels

(57) ABSTRACT

A disposable body fluids absorbent article including an absorbent core contained discrete particles, the discrete particles consisting of first polymer particles which have an initial water absorption rate and second polymer particles which have an initial water absorption rate lower than that of the first polymer particles, the first polymer particles being distributed exclusively in a zone defined by a lower ½ of a thickness of the core.

3 Claims, 2 Drawing Sheets

DISPOSABLE BODY FLUIDS ABSORBENT ARTICLE

BACKGROUND OF THE INVENTION

The present invention relates to body fluids absorbent articles such as disposable diapers, sanitary napkins and the like.

In such body fluids absorbent articles, it is well known to use discrete particles of a superabsorptive polymer as a component of the liquid-absorbent core. It is also well known that the discrete particles gelate and aggregate to form blocks.

The presence of the blocks prevent body fluids from transmitting and spreading within the absorbent core, resulting in deterioration of a body fluid absorbing capacity of the core, in spite of using the discrete particles. This tendency becomes more and more significant as a content of the discrete particles increases and/or an absorption rate increases.

SUMMARY OF THE INVENTION

In view of the above problem, it is an object of the invention to provide a body fluids absorbent article improved so that, even when the content of discrete particles of superabsorptive polymer in the core is relatively high and/or the absorption rate of the discrete particles is relatively high, the discrete particles can be utilized as efficiently as possible.

According to the present invention, there is provided a body fluids absorbent article including a liquid-pervious topsheet, a liquid-impervious backsheet and a liquid-absorbent core having a body-facing side and a garment-facing side and disposed therebetween the topsheet and the backsheet.

In the body fluids absorbent article, the core comprises 100~200 g/m² of fluff pulp, 20~45 g/m² of thermoplastic synthetic fibers and 120~400 g/m² of discrete particles of superabsorptive polymer; the fluff pulp and the synthetic fibers are present in an intermixed state so that their contents in the core gradually decrease from the body-facing side towards the garment-facing side in a thickness direction of the core; the discrete particles consists of 20~100 g/m² of first polymer particles presenting an initial water absorption rate V=40 or higher and 100~300 g/m² of second polymer particles presenting an initial water absorption rate V=5~20 wherein the initial water absorption rates are measured according to a measuring method described below; and a total amount of the first polymer particles is distributed in a lower zone adjacent the garment-facing side of the core thickness while 100~200 g/m² of the second polymer particles is distributed in an upper zone adjacent the body-facing side of the core and 0~100 g/m² of the second polymer particles is distributed in the lower zone of the core.

The initial water absorption rates (V) are measured by the following method:

(a) About 1 g of each polymer particles sample is put in a 250 mesh nylon cloth bag of 100 mm×200 mm and weighed. Thus a weight $W_0$ is obtained. This bag is immersed in an amount of 0.9% physiological saline solution poured into a 1 liter beaker;

(b) Bags taken out from the beaker in 10 seconds and 10 minutes of immersion, respectively, are suspended in midair for 10 minutes to drain. Thereafter these bags together with the contents are weighed and their weights $W_1$, $W_2$ are obtained; and (c) The initial water absorption rate V is calculated on the basis of an equation $$V=\{(W_1-W_0)/(W_2-W_0)\}\times 100$$

Preferably, the first polymer particles are concentrated on a bottom of the core and in vicinity thereof so that the first polymer particles may swell and aggregate after water absorption to form gel blocks spreading over the bottom of the core.

Preferably, the core has a thickness of 0.7~7 mm.

DETAILED DESCRIPTION OF THE PREFERRED EMBODIMENTS

Details of a body fluids absorbent article according to the present invention will be more fully understood from the description given hereunder with reference to the accompanying drawings.

Figure 1:
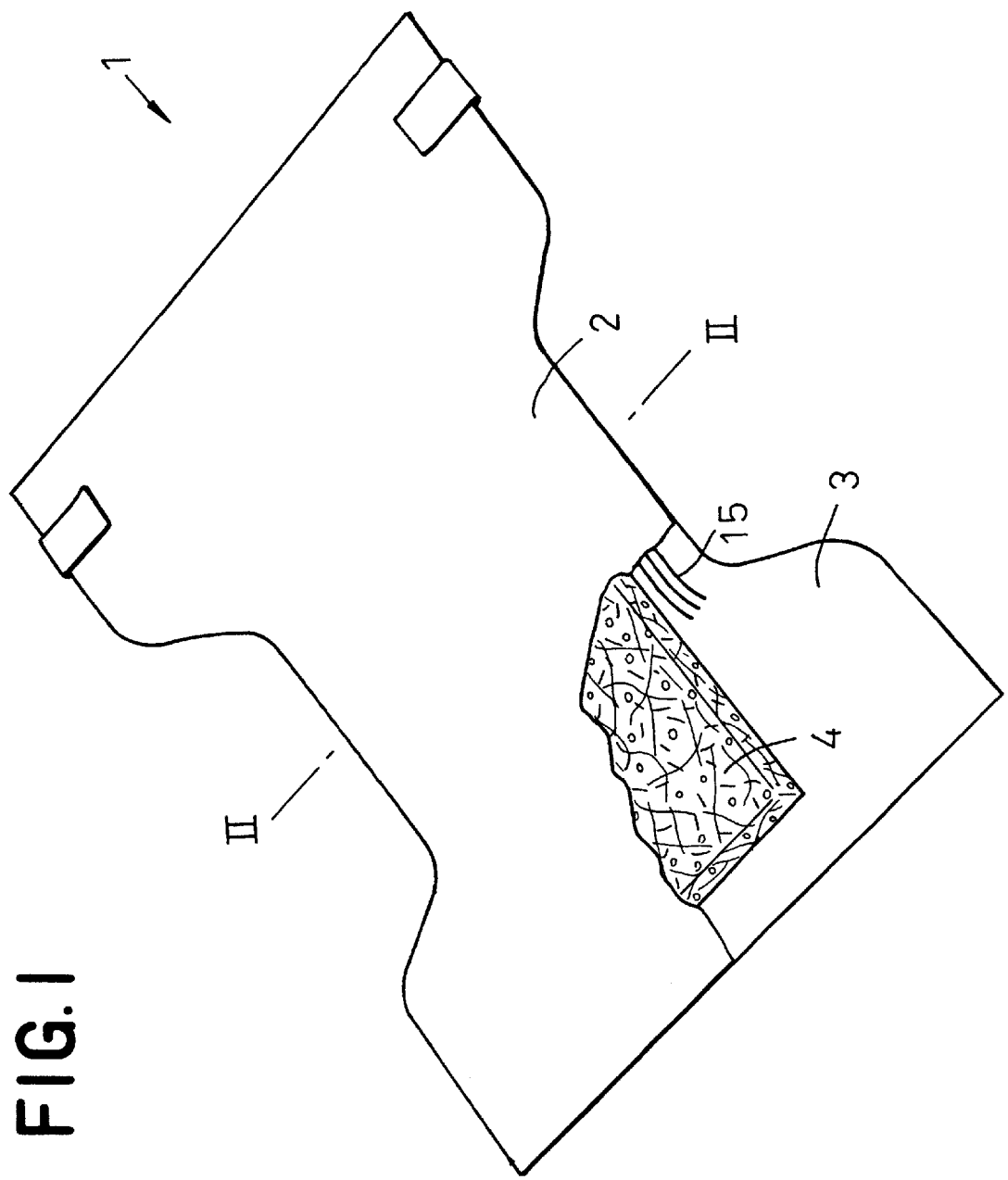
FIG. 1 is a perspective view of a diaper as a body fluids absorbent article constructed according to one embodiment of the present invention as partially broken away.

Disposable diaper 1 shown by FIG. 1 in a perspective view as partially broken away is an example of a body fluids absorbent article according to the present invention. The diaper 1 comprises a liquid-pervious topsheet 2, a liquid-impervious backsheet 3 and a liquid-absorbent core 4 disposed between these two sheets 2, 3. The topsheet 2 and the backsheet 3 are placed upon each other and joined together along their portions extending laterally beyond peripheral edges of the core 4. Elastic members 15 which to surround a wearer's legs extend along transversely opposite side edges of the diaper 1 and are secured under appropriate tension to an inner surface of at least one of the topsheet 2 and the backsheet 3.

Figure 2:
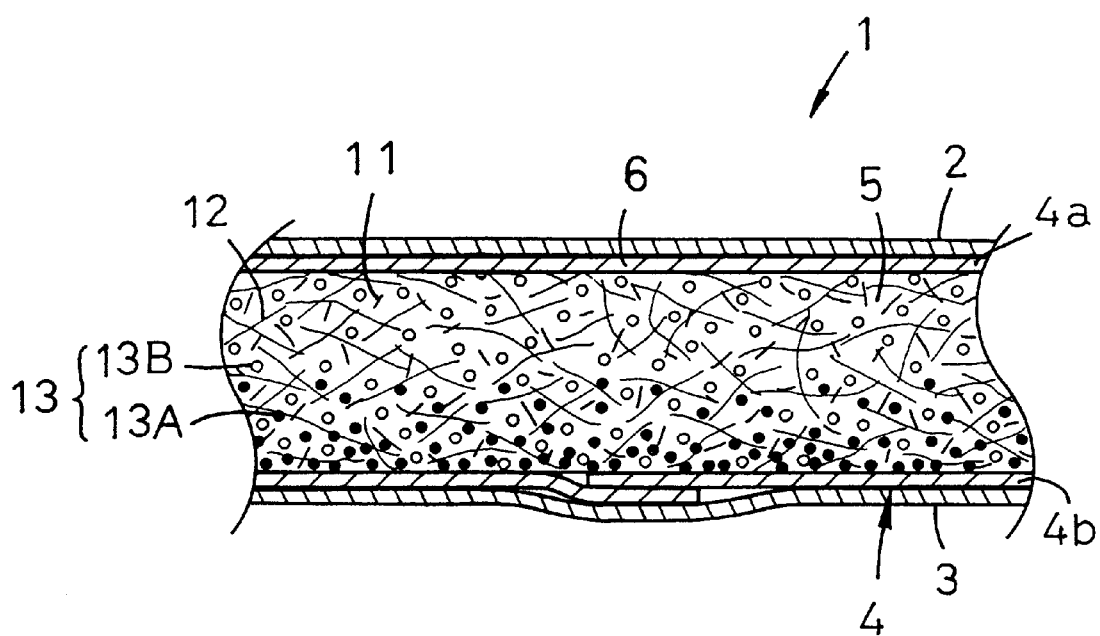
FIG. 2 is a fragmentary sectional view taken along line II—II in FIG. 1.

FIG. 2 is a fragmentary sectional view taken along line II—II in FIG. 1. As shown, the core has a body-facing side 4a and a garment-facing side 4b and is formed by covering a body fluids absorbent material 5 with tissue paper 6. The absorbent material 5 includes fluff pulp 11, thermoplastic synthetic fibers 12 and discrete particles 13 of superabsorptive polymer. A thickness of the core 4 except the tissue paper 6 is in a range of 0.7~7 mm, preferably in a range of 1~5 mm.

The fluff pulp 11 has a basis weight of 100~200 g/m² and its content distribution (% by weight) in a thickness direction of the core 4 progressively decreases from the body-facing side 4a towards the garment-facing side 4b.

Individual fibers of the thermoplastic synthetic fibers 12 are fused not only among themselves but also with the fluff pulp 11 and the discrete particles superabsorptive polymer 13 to maintain a shape of the core 4. To provide a desired effect, the thermoplastic synthetic fibers 12 having a relatively low melting point is mixed with the fluff pulp 11 and the discrete particles of superabsorptive polymer 13 preferably so that the thermoplastic synthetic fibers 12 may present its basis weight of 20~45 g/m². An example of such fibers 12 is split yarns obtained by splitting a three-layered laminate sheet of polyethylene/polypropyrene/polyethylene.

The discrete particles of superabsorptive polymer 13 are composed of first polymer particles 13A presenting a relatively high absorption rate and second polymer particles 13B presenting a relatively low absorption rate for body fluids or water. The first polymer particles 13A presents an initial water absorption rate V higher than 40, preferably higher than 50 as measured according to a measuring method of absorbed water as will be described in detail. The first polymer particle 13A are distributed at a ratio of 20~100 g/m² in a zone defined by a lower ½ of a thickness of the core and more preferably concentrated in proximity of a bottom of the absorbent material 5 constituting the core 4. Such concentrated distribution allows the first polymer particles 13A to be gelated, aggregated and thereby to form a block(s) spreading like a layer over a bottom surface of the core 4 after the first polymer particles 13A have absorbed body fluids. The second polymer particles 13B presenting an initial water absorption rate of 5~20 are distributed at a ratio of 100~200 g/m² in a zone defined by an upper ½ of a thickness of the core 4 and and at a ratio of 0~100 g/m² in a zone defined by the lower ½ of a thickness of the core 4, respectively. In the lower ½ zone, the second polymer particles 13B presenting the lower absorption rate are mixed with the first polymer particles 13A presenting the higher absorption rate, thereby inhibiting the formation of gel blocks due to gelation of the first polymer particles 13A alone and facilitating body fluids' entering into and passing through interfaces between the first polymer particles 13A and the second polymer particles 13B.

Measurement of Initial Water Absorption Rate

Initial water absorption rates V of the first and second polymer particles 13A, 13B are measured as follows:

(a) Polymer particles sample of about 1 g is put in a 250 mesh nylon cloth bag of 100 mm×200 mm and weighed. Thus a weight $W_o$ is obtained. After sealing, this bag is immersed in a sufficient amount of 0.9% physiological saline solution poured into a 1 liter beaker.

(b) Bags taken out from the beaker after immersion for 10 seconds and 10 minutes, respectively, are suspended in midair for 10 minutes to drain. Thereafter these bags together with the contends are weighed and their weights $W_1$, $W_2$ are obtained.

(c) The initial water absorption rate V is calculated on the basis of an equation as follows:

$$V=\{(W_1-W_o)/(W_2-W_o)\}\times 100$$

Calculated V represents a water absorption ratio in 10 seconds of immersion based on 100 representing the amount of absorbed water in 10 minutes of immersion. The present invention uses discrete particles of superabsorptive polymer of the type which can absorb an amount of water 40 or more times of the particles' own weight in 10 minutes of immersion and 70% or higher than the amount of absorbed water in saturated state. If a V-value of the particles is relatively high, it is indicated that the amount of absorbed water in 10 seconds of immersion is correspondingly high.

With the diaper 1 constructed as described above, a certain amount of body fluids are absorbed and held by the first polymer particles 13A as soon as the amount of body fluids arrive at the lower ½ zone of the core thickness. If the arrangement is adapted, in which the first polymer particles 13A are concentrated over the bottom of the absorbent material 5 constituting the core 4, the first polymer particles 13A aggregate together as they absorb the certain amount of body fluids and, in consequence, they form the layer-like gel block(s) spreading over the bottom. An additional amount of body fluids having transferred down and arrived later at the gel block(s) is prevented by it from further transferring down. Therefore, this additional amount of body fluids stays above the gel block(s) for a relatively long period. The amount of body fluids thus staying for a long period can be maintained in contact with the second polymer particles 13B presenting the relatively low absorption rate for a sufficiently long period to be absorbed by the polymer particles 13B. Accordingly, even when the total content of the polymer particles 13 is as high as 35~75% by weight, it is possible to achieve rapid absorption of body fluids as well as absorption of a large amount of water by efficiently utilizing the total content of the discrete particles superabsorptive polymer 13. The disposable diaper 1 adopting such core 4 can effectively alleviate leakage of body fluids.

Embodiment and Controls

1. Polymer particles of first and second types having characteristics indicated in Table 1 were used to make a disposable diapers.

TABLE 1

|  | Absorption in 10 sec $(W_1 - W_o)/P_0$ | Absorption in 10 min $(W_2 - W_o)/P_0$ | Initial absorption rate V $\{(W_1 - W_o)/(W_2 - W_o)\} \times 100$ |
|---|---|---|---|
| 1st polymer particles | 41.6 | 61.4 | 67.7 |
| 2nd polymer particles | 7.7 | 65.9 | 11.6 | wherein $P_0$: Weight of polymer particles before immersion $W_0$: Weight of a bag before immersion $W_1$: Weight of a bag in 10 sec. of immersion $W_2$: Weight of a bag in 10 min. of immersion 2. Absorbent material contained in the core was composed as indicated in Table 2.

TABLE 2

|  | Embodiment | Control 1 | Control 2 |
|---|---|---|---|
| Fluff pulp (g/m²) | 150 | 150 | 150 |
| Split yarns (g/m²) | 23 | 23 | 23 |
| 1st polymer particles (g/m²) | — | 50 | 50 |
| 2nd polymer particles (g/m²) | 250 | 200 | 200 |
| Distribution of 1st polymer particles | — | uniform | concentrated in lower ½ zone |
| Distribution of 2nd polymer particles | uniform | | |
| Core thickness (mm) | 2.5 | | |
| Core size (mm) | 100 × 400 | | |

3. Result of test

The respective cores were used to make the diapers as shown by FIG. 1 and 80 ml of artificial urine was poured twice onto each diaper at the interval of 10 minutes to measure times taken for absorption of artificial urine. Result of measurement is shown in Table 3.

TABLE 3

|  | Embodiment | Control 1 | Control 2 |
|---|---|---|---|
| Absorption rate (sec) for 1st pouring | 16 | 24 | 18 |

TABLE 3-continued

|                                  | Embodiment | Control 1 | Control 2 |
|----------------------------------|------------|-----------|-----------|
| Absorption rate (sec) for 2nd pouring | 15         | 20        | 29        |

As will be apparent from Table 3, the embodiment of the invention efficiently utilizes the polymer particles so that a high absorption rate can be maintained even when absorption of body fluids is repeated.

The disposable body fluids absorbent article according to the invention is characterized by the unique arrangement of the liquid-absorbent core, more particularly by composition of the discrete particles of superabsorptive polymer contained therein. Specifically, the polymer particles consisting of the polymer particles of first and second types presenting their initial absorption rates different from each other. The polymer particles of first type presenting a relatively high absorption rate are distributed in a lower ½ zone, preferably concentrated on a bottom of the core thickness. Most of the polymer particles of second type presenting a relatively low absorption rate are distributed in an upper ½ zone and mixed with the polymer particles of first type in said lower ½ zone. With a consequence, the polymer particles of both types can not readily form gel block except the bottom of the core. The core of such arrangement can achieve a high absorption rate as well as a large amount of absorption and the body fluids absorbent article adopting such core can effectively alleviate apprehensive leakage of body fluids.

What is claimed is:

1. A body fluids absorbent article comprising:

a liquid-pervious topsheet, a liquid-impervious backsheet and a liquid-absorbent core having a body-facing side and a garment-facing side and disposed between said liquid-pervious topsheet and said liquid-impervious backsheet, said core including about 100 to about 200 g/m$^2$ of fluff pulp, about 20 to about 45 g/m$^2$ of thermoplastic synthetic fibers and about 120 to about 400 g/m$^2$ of discrete particles of superabsorptive polymer, said fluff pulp and said synthetic fibers being present in an intermixed state so that the relative ratio of said fluff pulp and said synthetic fibers in said core gradually decreases from said body-facing side towards said garment-facing side in a thickness direction of the core, said polymer particles comprises about 20 to about 100 g/m$^2$ of first polymer particles which have an initial water absorption rate V of about 40 or higher, and about 100 to about 300 g/m$^2$ of second polymer particles which have and initial water absorption rate V of about 5 to about 20, and all of said first polymer particles are distributed in a lower zone adjacent said garment-facing side of said core while about 100 to about 200 g/m$^2$ of said second polymer particles are in an upper zone adjacent said body-facing side of said core and up to about 100 g/m$^2$ of said second polymer particles are distributed in said lower zone.

2. The article according to claim 1, wherein said first polymer particles are concentrated at a bottom of said core and in a vicinity thereof so that said first polymer particles swell and aggregate after water absorption and form a gel block spreading over said bottom of said core.

3. The article according to claim 1, wherein said core has a thickness of about 0.7 to about 7 mm.

* * * * *